US007236572B2

United States Patent
Maschke (10) Patent No.: US 7,236,572 B2
(45) Date of Patent: Jun. 26, 2007

(54) X-RAY IMAGING APPARATUS WITH CONTINUOUS, PERIODIC MOVEMENT OF THE RADIATION DETECTOR IN THE EXPOSURE PLANE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 51 days.

(21) Appl. No.: 10/856,228

(22) Filed: May 28, 2004

(65) Prior Publication Data

US 2005/0002486 A1    Jan. 6, 2005

(30) Foreign Application Priority Data

May 30, 2003  (DE)  ................. 103 24 911

(51) Int. Cl.
*G21K 5/10*  (2006.01)
(52) U.S. Cl. .................. 378/146; 378/62; 378/98.8
(58) Field of Classification Search ................. 378/62, 378/98.8, 146
See application file for complete search history.

(56) References Cited

U.S. PATENT DOCUMENTS

| 4,031,401 | A | * | 6/1977 | Jacob ...................... 378/146 |
| 4,228,357 | A | * | 10/1980 | Annis ........................ 378/62 |
| 4,398,302 | A | * | 8/1983 | Pfeiler ....................... 378/146 |
| 4,686,695 | A | * | 8/1987 | Macovski .................. 378/146 |
| 4,763,345 | A | * | 8/1988 | Barbaric et al. ........... 378/146 |
| 4,998,270 | A | * | 3/1991 | Scheid et al. .............. 378/155 |
| 5,526,394 | A | * | 6/1996 | Siczek et al. ............... 378/37 |
| 5,572,037 | A | * | 11/1996 | Liu et al. ................. 250/483.1 |
| 5,715,820 | A | * | 2/1998 | Stein et al. ................ 600/407 |
| 6,272,207 | B1 | * | 8/2001 | Tang ......................... 378/149 |
| 6,559,449 | B2 | | 5/2003 | Ikeda et al. |
| 6,614,872 | B2 | * | 9/2003 | Bueno et al. ............... 378/58 |

FOREIGN PATENT DOCUMENTS

| DE | 38 25 703 | 2/1990 |
| EP | 0 230 155 | 11/1985 |
| EP | 0 223 544 | 10/1993 |

* cited by examiner

*Primary Examiner*—Edward J. Glick
*Assistant Examiner*—Thomas R. Artman
(74) *Attorney, Agent, or Firm*—Schiff Hardin LLP

(57) ABSTRACT

An economical X-ray apparatus that allows a rapid exposure of comparatively large-format digital X-ray images has an exposure unit, with which a predetermined surface segment of an exposure plane can be exposed with X-ray radiation, and a digital X-ray detector that is moved in the exposure plane, with the X-ray detector being continuously periodically driven.

19 Claims, 4 Drawing Sheets

X-RAY IMAGING APPARATUS WITH CONTINUOUS, PERIODIC MOVEMENT OF THE RADIATION DETECTOR IN THE EXPOSURE PLANE

BACKGROUND OF THE INVENTION

1. Field of the Invention

The present invention relates to an X-ray apparatus of the type having an exposure unit by means of which a predetermined surface segment of an exposure plane can be exposed using X-ray radiation, and having a digital X-ray detector that can be moved in the exposure plane.

2. Description of the Prior Art

For years, most of the imaging examination methods used in medical technology have been based on X-ray images. In recent years, digital imaging techniques have increasingly become established, in place of conventional radiography based on photographic films. These digital techniques have the considerable advantage that the development of film, which is time-consuming, is not required. Rather, the image preparation takes place by means of electronic image processing. The image is therefore available immediately after the exposure. In addition, digital X-ray exposure techniques offer the advantage of improved image quality and possibilities for subsequent electronic image processing, as well as the possibility of a dynamic examination, i.e., the recording of moving X-ray images.

The digital X-ray exposure techniques that are conventionally used include systems known as image amplifier camera systems, based on television or CCD cameras, storage film or foil systems having an integrated or external readout unit, systems with optical coupling of a converter film to CCD cameras or a CMOS chip, selenium-based detectors with electrostatic readout, and solid-state detectors having active readout matrices with direct or indirect conversion of the X-ray radiation.

In particular, for the past several years solid-state detectors have been in development for digital X-ray imaging. These detectors are based on active readout matrices, made for example of amorphous silicon (a-Si), coated with an X-ray converter layer or scintillator layer, made of, for example, cesium iodide. The incident X-ray radiation is converted in the X-ray converter layer into visible light, which is converted into an electrical charge in photodiodes of the readout matrix, and stored in spatially-resolved fashion. Related technologies likewise use an active readout matrix made of amorphous silicon, but in combination with an X-ray converter (e.g. selenium) that converts the incident X-ray radiation directly into an electrical charge. This charge is then stored in spatially-resolved fashion on an electrode of the readout matrix. The stored charge is subsequently read out electronically via an active switching element, is converted into digital signals, and is sent to an electronic image processing system.

The basis of these solid-state detectors is conventionally semiconductor substrates (or semiconductor "plates"), as are produced in large quantities for consumer electronics applications, in particular for thin-film transistor display screens. Generally, however, such a semiconductor substrate manufactured for consumer electronics has only comparatively small dimensions (typically approximately 20×20 cm), which is often insufficient for medical applications. The manufacture of large-format semiconductor substrates, which would be suitable specifically for the sizes required in medical applications, is hardly possible at reasonable cost due to the relatively small piece counts involved. For X-ray detectors, it is therefore standard to cut a number of conventional semiconductor substrates and to glue them together to form a large substrate. This production method is still very complicated and therefore expensive.

German OS 38 25 703 discloses an X-ray apparatus having a strip-shaped digital detector element that is moved in linear fashion over the surface to be scanned during the exposure. After each shifting of the detector element, a partial image is recorded. The partial images are subsequently added together to form an overall image in an evaluation circuit.

Conventionally, in such a method the X-ray detector is moved in step-by-step fashion through the imaged surface (irradiated area). A disadvantage of this is that a considerable period of time is required for the detector to scan the entire imaged surface. In medical applications in particular, a short exposure time is often an essential criterion, especially since the patient under examination must generally hold himself or herself motionless for the duration of the exposure in order to avoid blurring of the image contours.

SUMMARY OF THE INVENTION

An object of the present invention is to provide an economical X-ray apparatus having a digital X-ray detector that enables a rapid exposure of comparatively large X-ray images.

This object is achieved in accordance with the invention by an X-ray apparatus having an exposure unit with which a predetermined surface segment of an exposure plane can be exposed with X-ray radiation, and an X-ray detector that can be moved in the exposure plane and that is continuously periodically driven. The term "continuously periodically driven" means that the X-ray detector is moved by a motor along a periodically repeating path, with this movement taking place continuously, i.e., in essentially uninterrupted fashion. In particular, a continuously periodic motion is understood to be an uninterrupted unidirectional motion along a closed path in the manner of a circle, or an otherwise uninterrupted oscillating motion between two points of reversal.

Because the X-ray detector is not moved in step-by-step fashion, but instead is moved in continuously periodic fashion, the time required in conventional systems for frequent braking and re-acceleration of the X-ray detector is saved. In this way, the exposure time is significantly reduced.

Preferably, the exposure unit is displaced and/or moved so that the surface segment is moved along the exposure plane synchronously with the X-ray detector. A "synchronous movement" of the surface segment to be exposed with respect to the X-ray detector is used herein to mean a periodic movement of the X-ray detector and movement of the exposed surface segment in-phase therewith (i.e., synchronous in the same direction), or is offset by half a phase angle (i.e., synchronous in the opposite direction), as a consequence of which the moved surface segment coincides with the moved X-ray detector at all times or at least at a number of locations in the exposure plane.

The synchronous movement of the surface segment with the X-ray detector has the result that only the area to be imaged is exposed to the X-ray radiation. The overall X-ray radiation exposure of a patient to be examined is reduced in this way.

The movement of the surface segment to be exposed in the exposure plane preferably takes place by the displacement of a diaphragm system connected downstream from an X-ray source of the exposure unit. Such a displaceable diaphragm system enables an especially simple, quasi-arbitrary, and quasi-instantaneous shifting of the surface segment to be exposed, especially since the diaphragm or diaphragms of the diaphragm system themselves have extremely low inertia and thus can be driven rapidly. Alternatively or in addition to displacing the surface segment, it is possible to move the overall exposure unit, i.e., the X-ray source and the diaphragm system.

In a preferred embodiment of the present invention, continuous periodic drive of the X-ray detector is achieved by the X-ray detector being driven rotationally around an axis of rotation oriented perpendicularly to the detection plane. In order to achieve a particularly good surface coverage, the axis of rotation preferably is situated at the edge of the detection surface. In particular, given a rectangular X-ray detector the axis of rotation preferably is situated in a corner of the detection surface.

In a structurally similar variant of the present invention, the X-ray detector is not driven so as to rotate in a circular motion, rotationally, but instead executes a rotating oscillating motion, with an angle of rotation of, preferably, >180° around the axis of rotation.

In another embodiment, the X-ray detector is fastened to a continuously driven conveyor band or belt, and thus is moved along the path of the conveyor band or belt continuously in one direction, on a closed loop path.

In another embodiment, the X-ray detector is driven with a translational oscillating motion; i.e., it oscillates along an essentially linear path in the exposure plane.

Preferably the motion of a movable diaphragm is matched to the motion of the X-ray detector, since in this way the exposed surface segment can be synchronized with the X-ray detector in a particularly simple fashion. Thus, if the X-ray detector is driven so as to circulate rotationally, the diaphragm preferably also is driven so as to circulate rotationally, etc. Matching of the type of motion of the diaphragm system to that of the X-ray detector, however, is not absolutely necessary. Thus, for example a detector driven rotationally with an oscillating motion could be combined with a diaphragm system oscillating in linear fashion, as long as the motion of the diaphragm system and the motion of the X-ray detector are synchronized in such a way that the surface segment defined by the diaphragm system coincides with the oscillating X-ray detector at a number of locations in the exposure plane. The X-ray apparatus is driven in such a way that the exposure of partial images takes place at locations at which the moved surface segment coincides with the moved X-ray detector. The partial segments of the exposure plane allocated to these partial images are oriented to one another so that the partial images can be combined in tiled fashion to form an overall image of the exposure plane. Depending on the type of motion of the X-ray detector and of the diaphragm system, the partial segments allocated to the partial images may overlap one another.

In order to reduce the overall exposure of the patient to X-ray radiation, the X-ray source of the exposure unit can be operated in pulsed fashion, so that the full X-ray power is emitted only at the exposure times, while the emitted X-ray power between the exposure times is reduced to a low level. This pulsed operation of the X-ray source can take place by variation of the power supplied to the X-ray source, or by the insertion of additional diaphragms into the beam path.

In order to produce the overall image from the exposed partial images, the X-ray apparatus preferably is equipped with an evaluation unit that combines the exposed partial images to form an overall image using electronic image processing.

Among advantages achieved by the present invention are in particular that at a comparatively low cost an X-ray apparatus is realized employing a digital exposure technology that enables the particularly rapid exposure of comparatively large-format images. By movement of the X-ray detector within the exposure plane, the exposure of large-format images is enabled using a comparatively small detector surface. This permits the use of economical X-ray detectors that can be manufactured using conventional semiconductor substrates such as those that are mass-produced for consumer electronics applications. The continuously periodic drive of the X-ray detector results in a significant acceleration of the exposure process, since the X-ray detector does not have to be braked and re-accelerated for each partial exposure. The synchronous movement of the surface segment to be exposed by displacement of the diaphragm system or the movement of the overall exposure unit has the advantage that only those regions of the exposure plane at which an exposure is supposed to take place are exposed to X-ray radiation. In particular, the described X-ray apparatus facilitates dynamic X-ray exposures, i.e., the recording of moving X-ray images.

DESCRIPTION OF THE PREFERRED EMBODIMENTS

Figure 1:
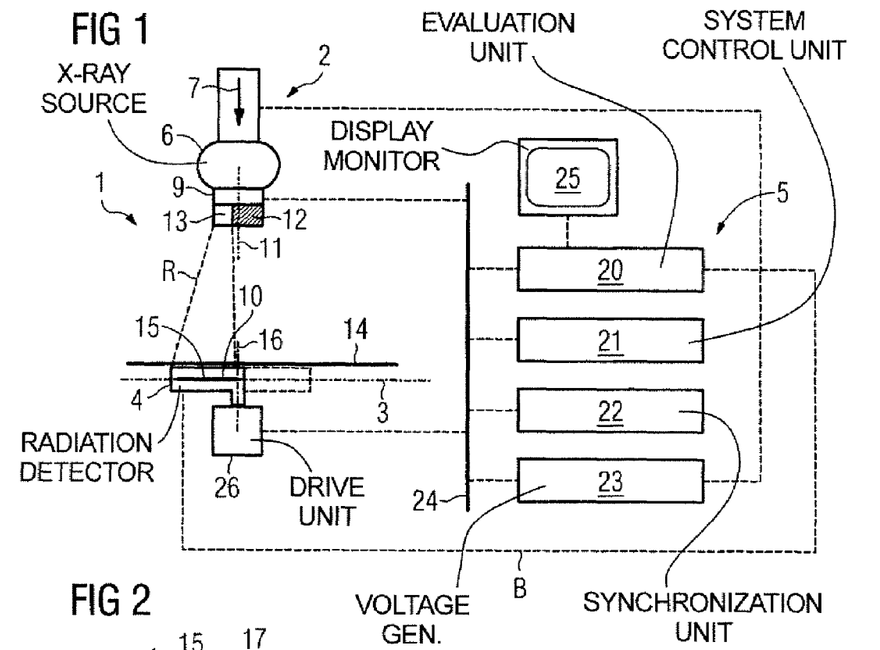
FIG. 1 is a schematic illustration of an X-ray apparatus having an exposure unit that has a rotating diaphragm, and having a digital X-ray detector that rotates in circular fashion, in accordance with the invention.

FIG. 1 shows an X-ray apparatus 1 having an exposure unit 2, an X-ray detector 4 situated in an exposure plane 3, and a control and evaluation system 5.

The exposure unit 2 includes an X-ray source 6 for producing a beam of X-ray radiation R. In the direction 7 of the radiation, a diaphragm system 9 is connected downstream from the X-ray source 6. In the diaphragm system 9, a portion of the X-ray radiation R is selected that strikes an exposure plane 3 within a predetermined surface segment 10. As a result, the surface segment 10 is exposed by the X-ray radiation R. The remaining X-ray radiation R produced by X-ray source 6 is absorbed by the diaphragm system 9 in order to avoid undesirable scatter radiation. The area of exposure plane 3 situated outside surface segment 10 is thus largely blocked from the X-ray radiation R.

The diaphragm system 9 includes a diaphragm 12 that can be rotated around an axis of rotation 11, and that has a diaphragm aperture 13 that is transparent to the X-ray radiation R. As is described in more detail below, when the diaphragm 12 is in rotation, the diaphragm aperture 13 is moved around axis 11 of rotation along a circular path. In this way, the portion of the X-ray radiation R that is let through by the diaphragm aperture 13 also moved in relation to the exposure plane 3, so the exposed surface segment 10 likewise moves along a circular path in the exposure plane 3.

Between the exposure unit 2 and the X-ray detector 4 there is situated an exposure table 14 on which a patient or object to be examined (not shown) can be brought into the desired exposure position. The X-ray image of the patient or object to be examined is projected into the exposure plane 3 and is acquired by the X-ray detector 4 when the X-ray radiation R is activated.

Differing from the representation according to FIG. 1, the X-ray apparatus 1 can be situated so that the direction of radiation 7 proceeds horizontally. In this case, instead of the X-ray table 14 a vertical plate (not shown) or suitable support elements may be provided for fixing the patient or object to be examined.

The X-ray detector 4 is a flat, digital solid-state detector having a rectangular detection surface 15 whose dimensions and geometry corresponding essentially to the exposed surface segment 10. The X-ray detector 4 preferably is equipped with an active readout matrix made of amorphous silicon (a-Si). With respect to the dimensions of the detection surface 15, the X-ray detector 4 is matched to measurements that are standard for semiconductor matrices used in consumer electronics. Such dimensions can be, in particular, 21.5 cm×21.5 cm, 29 cm×39 cm, etc.

Figure 2A:
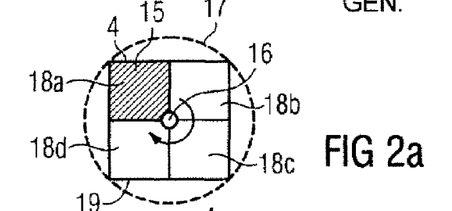
FIGS. 2a–2f are schematic top views of three chronologically successive rotational positions of the X-ray detector according to FIG. 1, as well as respectively simultaneous rotational positions of the diaphragm.

For most medical applications, an exposure format is required that exceeds the above-identified dimensions of the detection surface 15 (e.g., 43 cm×43 cm). In order to enlarge the achievable exposure format of X-ray apparatus 1 without actually enlarging the detection surface 15, the X-ray detector 4 is mounted so as to be capable of rotational motion around an axis of rotation 16 in the exposure plane 3. As can also be seen in FIGS. 2a and 2e, the axis of rotation 16, which is oriented perpendicularly to the detection surface 15, intersects a corner point of the approximately square X-ray detector 4. When the X-ray detector 4 rotates around the axis of rotation 16, the detection surface 15 thus passes over the surface of a circle 17 having a radius corresponding to the diagonals through the detection surface 15. In particular, as can be seen in FIGS. 2a, 2c, 2e, four partial segments 18a, 18b, 18c, 18d can be inscribed in the circle 17, each having the dimensions of detection surface 15. Partial segments 18a–18d are tiled with one another in such a way that they form the quadrants of an overall segment 19 in the shape of a square, having an edge length that is twice that of the detection surface 15.

Figure 2B:
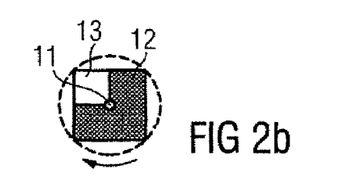
Figure 2C:
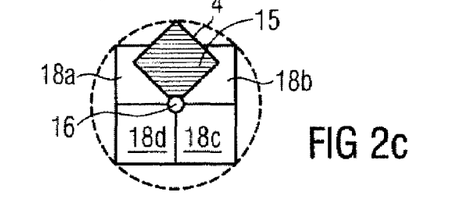
Figure 2D:
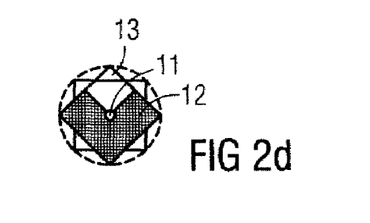
Figure 2E:
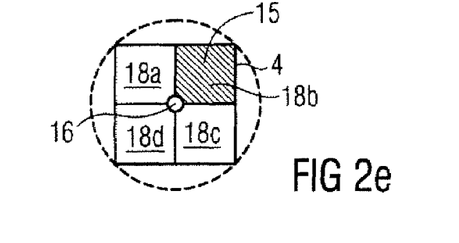
Figure 2F:
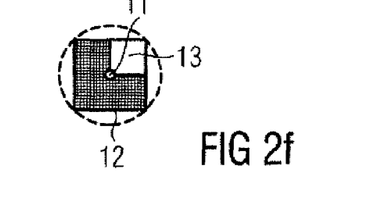

As can be seen from FIGS. 2b, 2d, 2f, the diaphragm 12 essentially has the shape of a centrically rotationally mounted square. The diaphragm aperture 13 here forms a quadrant having the aforementioned square shape.

The control and evaluation system 5 of the X-ray apparatus 1 includes an image processing evaluation unit 20, a system control unit 21, a synchronization unit 22, and a voltage generator 23, which communicate via a data and system bus 24. For visualization of the X-ray exposure, the evaluation unit 20 is connected to an output apparatus, in particular a display monitor 25.

For the operation of X-ray apparatus 1, the X-ray radiation R is activated by activating the voltage generator 23 and the X-ray source 6 driven thereby. In addition, the diaphragm 12 and the X-ray detector 4 are set into circulating rotation. The synchronization unit 22 synchronizes a drive 26 for the X-ray detector 4 and the drive (not shown) for the diaphragm 12 in such a way that the exposed surface segment 10 always coincides with the detection surface 15, independent of the rotational position of the X-ray detector 4.

As is illustrated in FIGS. 2a–2f, this is achieved by, as viewed along the direction of radiation 7, i.e., parallel to axes of rotation 16 and 11, the detection surface 15 is always oriented rotationally in the same way as is diaphragm aperture 13. FIGS. 2a, 2b show such corresponding positions of the X-ray detector 4 and of the diaphragm 12 at a first point in time. Here, in analogy to the position of the hands of a standard analog clock, detection surface 15 and diaphragm aperture 13 are situated approximately in a "10:30" position. In this position, the X-ray detector 4 records a first partial image corresponding to partial segment 18a. The image data B are read out electronically from the X-ray detector 4 and are supplied to the evaluation unit 20.

FIGS. 2c, 2d show an intermediate position of the X-ray detector 4 and the diaphragm 12 at a later point in time, at which the detection surface 15 and the diaphragm aperture 13 are oriented in a "12 o'clock" position.

FIGS. 2e and 2f show corresponding positions of the detection surface 15 and the diaphragm aperture 13 at a still later point in time, at which the detection surface 15 and diaphragm aperture 13 are synchronously rotated into a "1:30" position. Here, in particular the detection surface 15 coincides completely with the partial segment 18b. In this position, a second partial image corresponding to the partial segment 18b is recorded, and the associated image data B are supplied to the evaluation unit 20.

As time continues to elapse, due to the continuing rotation of the X-ray detector 4 the detection surface 15 first comes (in a manner not shown in more detail) into complete coincidence with partial segment 18c, and then into complete coincidence with partial segment 18d. In each of the two last-named positions, a partial image corresponding respectively to partial segments 18c or 18d is also recorded and is supplied to the evaluation unit 20.

In the evaluation unit 20, the four partial images are combined, using electronic image processing, to form an overall image that corresponds to the X-ray image projected into the overall segment 19 of exposure plane 3. This overall image is displayed on the display monitor 25.

It is essential that the X-ray detector 4 circulate continuously, i.e., it continues to rotate during the exposure of the partial images. This saves time that is conventionally used for the braking and re-acceleration of X-ray detector 4. In comparison to this, the exposure method according to the present invention is considerably accelerated. In order to improve the image quality, it is possible to repeatedly record the partial images corresponding to the individual partial segments 18a–18d over a number of rotations of the X-ray detector 4, and to superpose the repeated exposures of the individual partial images on one another. Preferably, no exposure takes place in the intermediate positions of the X-ray detector 4, as shown for example in FIG. 2c. In order to reduce the overall radiation exposure due to the X-ray radiation R, the X-ray source 6 preferably is operated in pulsed fashion, so that it emits the full radiation power only during the exposure times, i.e., only when the X-ray detector 4 passes over one of the partial segments 18a to 18d. In the intermediate times, X-ray source 6 supplies only a comparatively low level of radiation. It is alternatively possible to record intermediate exposures in arbitrary intermediate positions of the X-ray detector 4, and to superpose these in order to improve the image quality of the overall image.

The system control unit 21 handles general control functions as well as the coordination of the individual hardware components of the X-ray apparatus 1. In addition, it contains software for the operation of the X-ray apparatus 1.

Figure 3:
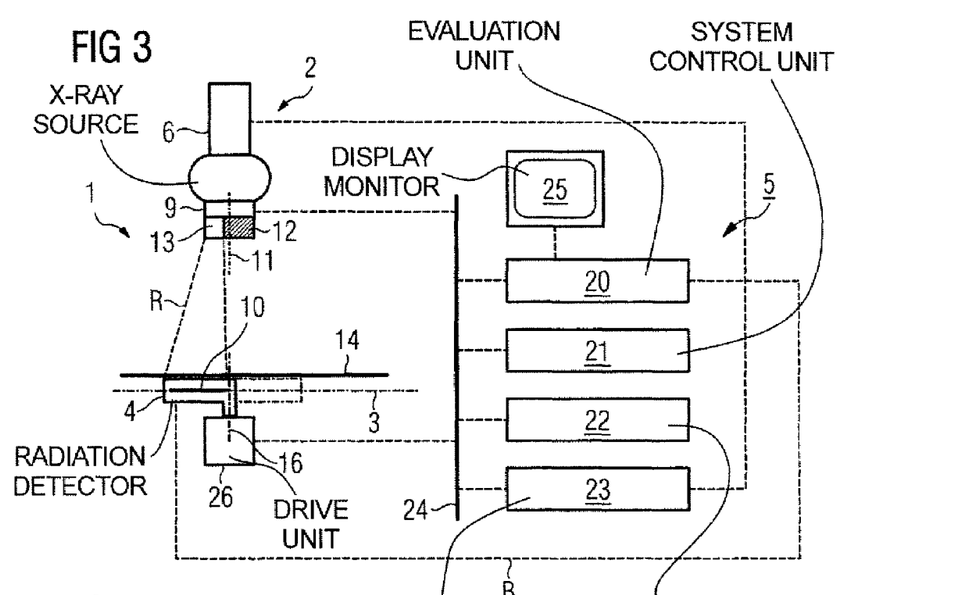
FIG. 3 is a schematic illustration of a further embodiment of the inventive X-ray apparatus, having an X-ray detector that is rotationally driven in oscillating fashion, and a diaphragm that is rotationally driven in oscillating fashion.

An alternative embodiment of the X-ray apparatus 1 is shown in FIG. 3. This embodiment differs from the embodiment described above in that X-ray detector 4 is not driven so as to circulate in rotational fashion, but rather, in a manner similar to the windshield wiper of a motor vehicle, is pivoted around axis of rotation 16 within an angle of approximately 220 E. Within this angle of rotation, the X-ray detector 4 executes a continuous pendulum or oscillating motion. As can be seen from FIG. 4a–4f, during the oscillating motion the detection surface 15 of the X-ray detector 4 passes over the surface of a segment 27 of a circle within the exposure plane 3, in which two partial segments 18a, 18b having the dimensions of the detection surface 15 can be inscribed. The partial segments 18a, 18b lie side-by-side next one another, and when combined yield an overall segment 19.

As can be seen in FIGS. 4a–4f, the diaphragm 12 is also rotationally driven so as to oscillate through an angle of rotation of approximately 220 E. The motions of the X-ray detector 4 and the diaphragm 12 are synchronized by the synchronization unit 22 so that the exposed surface segment 10 always coincides with the detection surface 15 of the oscillating X-ray detector 4.

The embodiment described above resembles the realization of the X-ray apparatus 1 according to FIG. 3 in that the exposure of a partial image always takes place when the detection surface 15 of X-ray detector 4 passes over one of the partial segments 18a and 18b. The partial images are in turn combined with one another in the evaluation unit 20 by electronic image processing, and are displayed on the display monitor 25. In the embodiment according to FIG. 3, the motion of the X-ray detector 4 is continuous insofar as the X-ray detector 4 comes to rest briefly only at the reversal points of the oscillation path, for the purpose of reversing the direction of motion. In contrast, the X-ray detector 4 preferably passes the exposure locations, i.e., partial segments 18a and 18b, without braking. Braking or acceleration of the X-ray detector 4 takes place only in the two end zones 28a and 28b of the circle segment 27, which extend past a semicircle.

Figures 4, 4A:
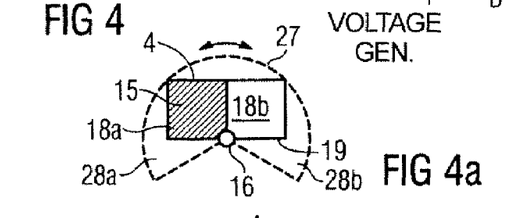
FIGS. 4a–4f are schematic views of three chronologically successive rotational positions of the X-ray detector according to FIG. 3, as well as associated positions of the diaphragm.
Figure 4B:
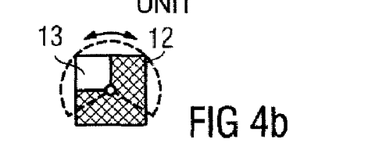
Figure 4C:
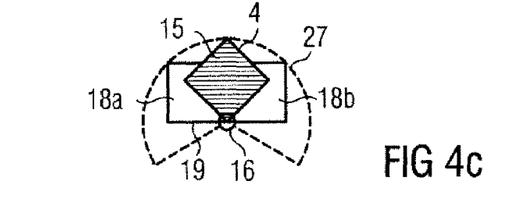
Figure 4D:
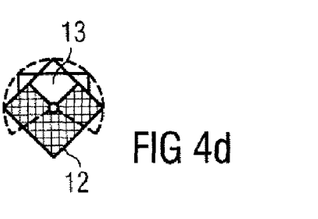
Figure 4E:
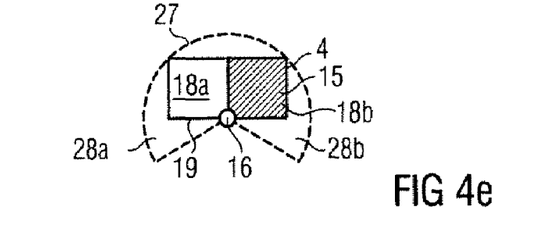
Figure 4F:
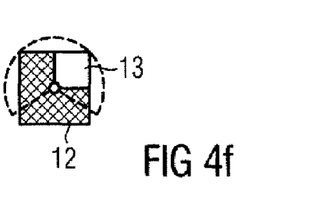

Analogous to FIGS. 2a–2f, FIGS. 4a–4f show corresponding rotational positions of the X-ray detector 4 and the diaphragm 12 at three successive points in time. FIGS. 4a and 4b correspond to a first point in time, at which a first partial image is recorded. FIGS. 4c and 4d indicate an intermediate position of the X-ray detector 4 or the diaphragm 12. In FIGS. 4e and 4f, both the detection surface 15 and the diaphragm aperture 13 are rotated into a "1:30" position, so that the detection surface 15 coincides with second partial segment 18b. After the X-ray detector 4 has passed the last position, in which the second partial image 18b is recorded, it is braked in the end zone 28b, and travels the path described in FIGS. 4a to 4e in the reverse direction. The same holds for the diaphragm 12.

Figure 5:
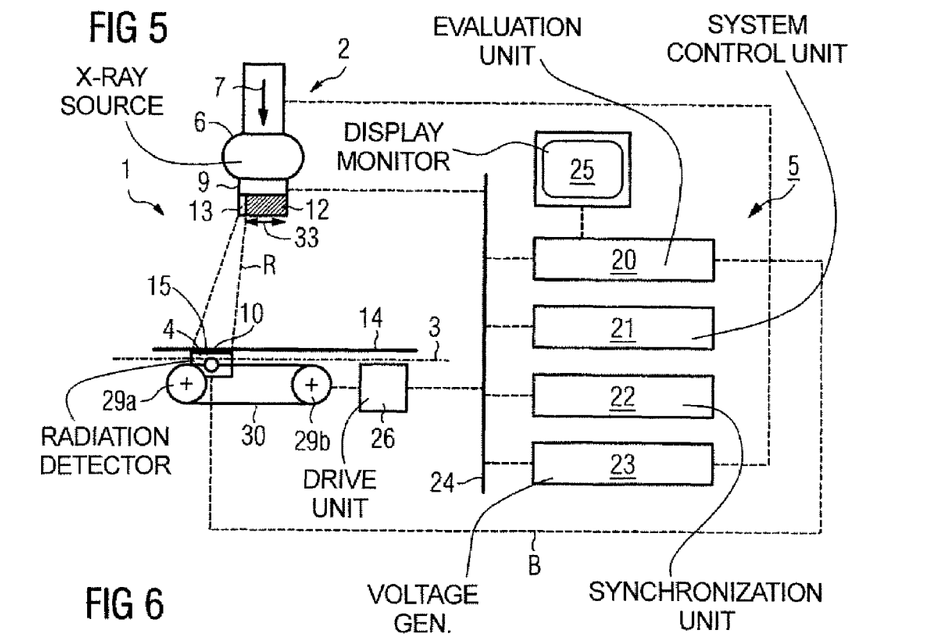
FIG. 5 is a schematic illustration of a further embodiment of the inventive X-ray apparatus, having an X-ray detector that is driven in unidirectional fashion along a closed path by a conveyor belt, and having a diaphragm system that has a slit diaphragm that can be displaced in linear fashion.
Figure 6A:
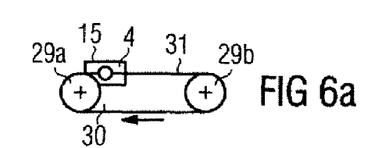
FIGS. 6a–6h are schematic top views of four chronologically successive translational positions of the X-ray detector according to FIG. 5, as well as associated positions of the slit diaphragm.
Figure 6B:
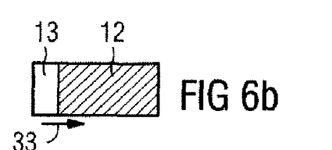
Figure 6C:
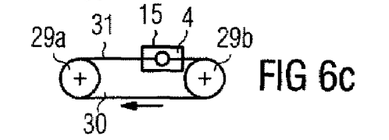
Figure 6D:
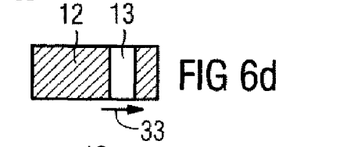
Figure 6E:
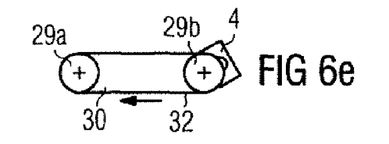
Figure 6F:
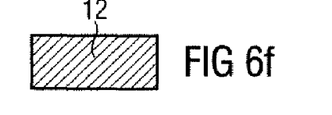
Figure 6G:
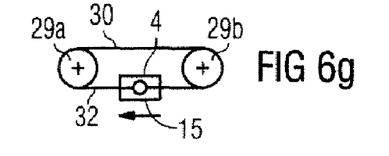
Figure 6H:
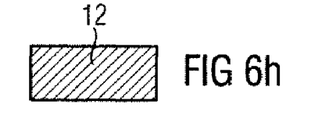

In an additional embodiments of the X-ray apparatus 1, shown in FIGS. 5 and 6, the X-ray detector 4 is coupled, for the purpose of being driven, to a conveyor belt 30 that is trained around two drive rollers 29a and 29b. The conveyor belt 30 is driven by drive unit 26 continuously in one direction. As can be seen from the sequence of FIGS. 6a, 6c, 6e 6g, the X-ray detector 4, following the path of conveyor belt 30, first moves, on the upper side 31 of the belt, within the exposure plane 3 toward drive roller 29b, and is subsequently carried over the periphery of the drive roller 29b to the lower side 32 of the belt, and is there conveyed back in the direction of the drive roller 29a.

In the embodiment of the X-ray apparatus 1 shown in FIGS. 5 to 6 as well, the exposed surface segment 10 is also carried along with the detection surface 15 of the X-ray detector 4 by the displacement of the diaphragm system 9, to the extent that this is possible. For this purpose, the diaphragm 12 is provided with a slit-shaped diaphragm aperture 13 that can be displaced in a direction 33 parallel to the orientation of conveyor belt 30, i.e., perpendicular to the direction 7 of radiation. This can be seen from the sequence of FIGS. 6b, 6d, 6f, 6h. As long as the X-ray detector 4 is conveyed on the belt upper side 31, diaphragm aperture 13 is by the synchronization unit 22 in the direction 33 so that the exposed surface segment 10 always coincides with the detection surface 15. Partial images are thereby recorded at sufficiently close time intervals and are supplied to the evaluation unit 20, where they are combined to form an overall image. Because an image exposure is not possible as long as the X-ray detector 4 is being carried back on the lower side 32 of the belt 30 (according to FIGS. 6e, 6g), during this time the diaphragm 12 preferably is completely closed in order to avoid unnecessary radiation exposure.

Figure 7:
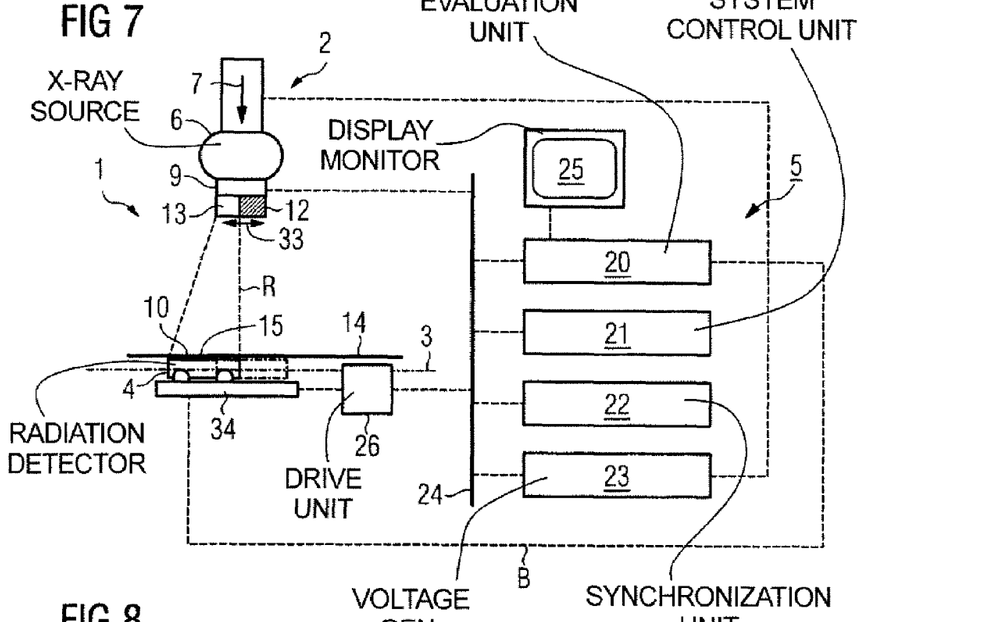
FIG. 7 is a schematic illustration of a further embodiment of the inventive X-ray apparatus, in which the X-ray detector is driven so as to oscillate in linear fashion, and having a diaphragm that can be displaced in linear fashion.

In a further embodiment of X-ray apparatus 1, shown in FIG. 7, the X-ray detector 4 is mounted on a slide rail 34, and, driven by a drive unit 26, executes a linear translational oscillating motion in the exposure plane 3.

For synchronization of the exposed surface segment 10 with the detection surface 15, the diaphragm 12 can be moved, as in the embodiment according to FIG. 5, along a direction 33 that is perpendicular to the direction 7 of radiation R. The displacement of the diaphragm 12 can take place, as in FIG. 5 and FIG. 6, synchronously in the same direction with the motion of the X-ray detector 4, with a slit-shaped diaphragm aperture 13 being tracked with the detection surface 15.

Figures 8, 8A:
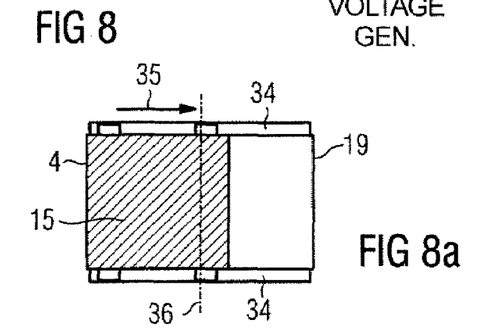
FIGS. 8a–8d are schematic top views of two chronologically successive oscillation positions of the X-ray detector according to FIG. 7, as well as associated positions of the diaphragm.
Figure 8B:
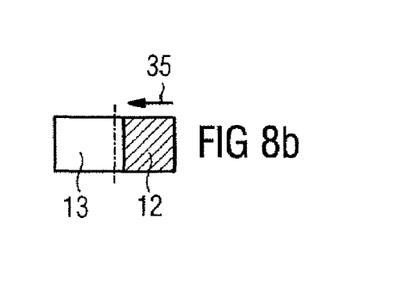
Figure 8C:
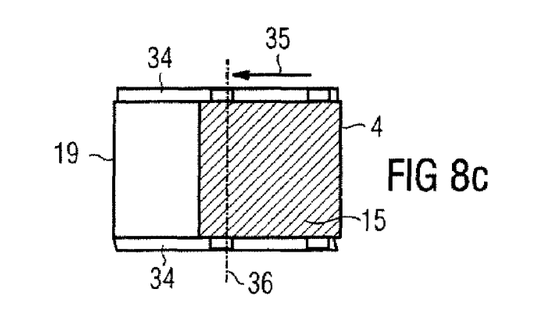
Figure 8D:
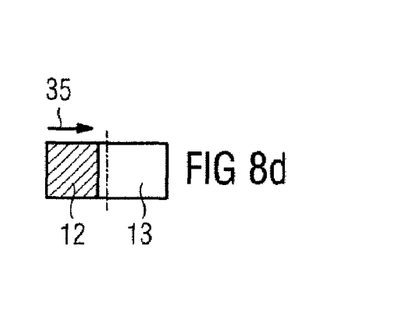

Alternatively, the diaphragm 12 can be moved synchronously in the opposite direction with the X-ray detector 4. This is illustrated in more detail in FIGS. 8a and 8c, which show X-ray detector 4 in the vicinity of the two points of reversal of the oscillating motion. The position of the diaphragm 12 corresponding to FIG. 8a is shown in FIG. 8b. The diaphragm position corresponding to the position of the X-ray detector 4 according to FIG. 8c is shown in FIG. 8d. In all FIGS. 8a to 8d, arrows 35 indicate the motion of the X-ray detector 4 or of the diaphragm 12.

Both in the first position of the X-ray detector 4 and the diaphragm 12 according to FIGS. 8a and 8b, and in the second position according to FIGS. 8c and 8d, the detection surface 15 and the diaphragm aperture 13 have the same orientation, whereby the X-ray detector 4 is completely exposed, and the surface segment 10 therefore coincides with the detection surface 15. In each of these two positions, a partial image is recorded and the image data B are supplied to evaluation unit 20. As can be seen from FIGS. 8a and 8c, in the two positions the detection surface 15 protrudes past the center line 36 (indicated as a broken line) of the pivot path of the X-ray detector 4. Correspondingly, the partial images recorded in the two positions of the X-ray detector 4 overlap one another. These partial images are superposed in evaluation unit 20 so that an overall image of the exposure plane 3 results that has no gaps and that corresponds to the overall segment 19.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray apparatus comprising:
   an X-ray exposure unit for exposing a predetermined surface segment of an exposure plane with X-rays;
   a digital flat panel X-ray detector, having a rectilinear detector region with a detector size that is active to simultaneously detect said X-rays anywhere within said detector region along two directions of said detector region perpendicular to one another;
   a drive arrangement connected to said digital flat panel X-ray detector for moving an entirety of said flat panel X-ray detector, and thus an entirety of said detector region, in a continuously periodic motion to detect said x-rays within a rectilinear area larger than said detector size; and
   a displacement unit connected to said exposure unit for moving said exposure unit for displacing said surface segment synchronously with said X-ray detector in said exposure plane.

2. An X-ray apparatus as claimed in claim 1 wherein said exposure unit comprises an X-ray source for emitting an X-ray beam and a diaphragm system disposed in a propagation path of said X-ray beam, said diaphragm system having a diaphragm movable perpendicular to said propagation path for gating said X-ray beam to set a size of said surface segment.

3. An X-ray apparatus as claimed in claim 1 wherein said drive arrangement moves said X-ray detecotr in said continuosly periodic motion by traslation oscillating said X-ray deteector.

4. An X-ray apparatus as claimed in claim 1 wherein said X-ray detector, during said continuous periodic motion, produces a plurality of partial images respectively obtained at different positions of said X-ray detector in said continuous periodic motion, and wherein said X-ray apparatus comprises an evaluation unit supplied with said partial images for forming an overall complete image from said partial images.

5. An X-ray apparatus comprising:
   an X-ray exposure unit for exposing a predetermined surface segment of an exposure plane with X-rays, said detector region having an edge and a detector surfaces;
   a digital flat panel X-ray detector, having a rectilinear detector region with a detector size that is active to simultaneously detect said X-rays anywhere within said detector region alona two directions of said detector region perpendicular to one another; and
   a drive arrangement connected to said digital flat panel X-ray detector for moving an entirety of said flat panel X-ray detector, and thus an entirety of said detector region, in a continuously periodic motion to detect said x-rays within a rectilinear area larger than said detector size, said drive arrangement moving said X-ray detector in said continuously periodic motion by rotating said X-ray detector in a single circular direction around an axis of rotation, said axis of rotation being disposed substantially at said edge of said detector region and being perpendicular to said detection surface.

6. An X-ray apparatus as claimed in claim 5 wherein said exposure unit comprises an X-ray source for emitting an X-ray beam and a diaphragm system disposed in a propagation path of said X-ray beam, said diaphragm system having a diaphragm movable perpendicular to said propagation path for gating said X-ray beam to set a size of said surface segment.

7. An X-ray apparatus as claimed in claim 5 wherein said X-ray detector, during said continuous periodic motion, produces a plurality of partial images respectively obtained at different positions of said X-ray detector in said continuous periodic motion, and wherein said X-ray apparatus comprises an evaluation unit supplied with said partial images for forming an overall complete image from said partial images.

8. An X-ray apparatus comprising:
   an X-ray exposure unit for exposing a predetermined surface segment of an exposure plane with X-rays, said detector region having an edge and a detection surface;
   a digital flat panel X-ray detector, having a rectilinear detector region with a detector size that is active to simultaneously detect said X-rays anywhere within said detector region along two direction of said detector region perpendicular to one another; and
   a drive arrangement connected to said digital flat panel X-ray detector for moving an entirety of said flat panel X-ray detector, and thus an entirety of said detector region, in continuously periodic motion to detect said x-rays within a rectilinear area larger than said detector size, said drive arrangement moving said X-ray detector in said continuous periodic motion by oscillating said detector region around an axis of rotation, said axis of rotation being situated substantially at said edge of said detector region and being perpendicular to said detection surface.

9. An X-ray apparatus as claimed in claim 8 wherein said exposure unit comprises an X-ray source for emitting an X-ray beam and a diaphragm system disposed in a propagation path of said X-ray beam, said diaphragm system having a diaphragm movable perpendicular to said propagation path for gating said X-ray beam to set a size of said surface segment.

10. An X-ray apparatus as claimed in claim 8 wherein said X-ray detector, during said continuous periodic motion, produces a plurality of partial images respectively obtained at different positions of said X-ray detector in said continuous periodic motion, and wherein said X-ray apparatus comprises an evaluation unit supplied with said partial images for forming an overall complete image from said partial images.

11. An X-ray apparatus comprising:
an X-ray exposure unit for exposing a predetermined surface segment of an exposure plane with X-rays;
a digital flat panel X-ray detector, having a rectilinear detector region with a detector size that is active to simultaneously detect said X-rays anywhere within said detector region along two directions of said detector region perpendicular to one another; and
a drive arrangement connected to said digital flat panel X-ray detector for moving an entirety of said flat panel X-ray detector, and thus an entirety of said detector region, in a continuously periodic motion to detect said x-rays within a rectilinear area larger than said detector size, said drive arrangement comprising a conveyor belt and moving said X-ray detector in said continuous periodic motion by unidirectionally moving said X-ray detector along a closed loop path of said conveyor belt.

12. An X-ray apparatus as claimed in claim 11 wherein said exposure unit comprises an X-ray source for emitting an X-ray beam and a diaphragm system disposed in a propagation path of said X-ray beam, said diaphragm system having a diaphragm movable perpendicular to said propagation path for gating said X-ray beam to set a size of said surface segment.

13. An X-ray apparatus as claimed in claim 11 wherein said X-ray detector, during said continuous periodic motion, produces a plurality of partial images respectively obtained at different positions of said X-ray detector in said continuous periodic motion, and wherein said X-ray apparatus comprises an evaluation unit supplied with said partial images for forming an overall complete image from said partial images.

14. An X-ray apparatus comprising:
an X-ray exposure unit for exposing a perdetermined surface segment of an exposure plane with X-rays, said exposure unit comprising an X-ray source for emitting an X-ray beam propagting in beam direction, and a diaphram system having a diaphram movable perpendicularly to said beam direction for gating said X-ray beam to set a position of said surface segment;
a digital flat panel X-ray detector, having a rectilinear detector region with a detector size that is active to simultaneously detect said X-rays anywhere within said detector region along two directions of said detector region perpendicular to one another;
a drive arrangement connected to said digital flat panel X-ray detector for moving an entirety of said flat panel X-ray detector, and thus an entirety of said region, in a continuously periodic motion to detect said x-rays within a rectilinear area larger than said detector size; and
a displacement unit connected to said diaphram system for moving said diaphram in a continuously periodic motion identical to the continuously periodic motion of said X-ray detector.

15. An X-ray apparatus as claimed in claim 14 wherein said exposure unit comprises an X-ray source for emitting an X-ray beam and a diaphragm system disposed in a propagation path of said X-ray beam, said diaphragm system having a diaphragm movable perpendicular to said propagation path for gating said X-ray beam to set a size of said surface segment.

16. An X-ray apparatus as claimed in claim 14 wherein said X-ray detector, during said continuous periodic motion, produces a plurality of partial images respectively obtained at different positions of said X-ray detector in said continuous periodic motion, and wherein said X-ray apparatus comprises an evaluation unit supplied with said partial images for forming an overall complete image from said partial images.

17. An X-ray apparatus comprising:
an X-ray exposure unit for exposing a predetermined surface segment of an exposure plane with X-rays;
a digital flat panel X-ray detector, having a rectilinear detector region with a detector size that is active to simultaneously detect said X-rays anywhere within said detector region along two directions of said detector region perpendicular to one another; and
a drive arrangement connected to said digital flat panel X-ray detector for moving an entirety of said flat panel X-ray detector, and thus an entirety of said detector region, in a continuously periodic motion to detect said x-rays within a rectilinear area larger than said detector size, said drive arrangement, by moving said X-ray detector in said continuously periodic motion, causing said X-ray detector to, at times, not coincide with said surface segment, and said exposure unit comprising an X-ray source and a voltage generator for driving said X-ray source, said voltage generator driving said X-ray source in a pulsed manner for causing said X-ray source to emit X-rays at a first power outside of said times and at a second power within said times, said second power being lower than said first power.

18. An X-ray apparatus as claimed in claim 17 wherein said exposure unit comprises an X-ray source for emitting an X-ray beam and a diaphragm system disposed in a propagation path of said X-ray beam, said diaphragm system having a diaphragm movable perpendicular to said propagation path for gating said X-ray beam to set a size of said surface segment.

19. An X-ray apparatus as claimed in claim 17 wherein said X-ray detector, during said continuous periodic motion, produces a plurality of partial images respectively obtained at different positions of said X-ray detector in said continuous periodic motion, and wherein said X-ray apparatus comprises an evaluation unit supplied with said partial images for forming an overall complete image from said partial images.

* * * * *